United States Patent
Morimoto et al.

(10) Patent No.: US 10,485,759 B2
(45) Date of Patent: Nov. 26, 2019

(54) JELLY FOR ASSISTING IN TAKING DRUG

(71) Applicant: MORIMOTO-PHARMA CO., LTD., Osaka-shi, Osaka (JP)

(72) Inventors: Shuji Morimoto, Osaka (JP); Masao Nozaki, Osaka (JP)

(73) Assignee: MORIMOTO-PHARMA CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/668,698

(22) Filed: Aug. 4, 2017

(65) Prior Publication Data

US 2017/0326068 A1    Nov. 16, 2017

Related U.S. Application Data

(63) Continuation of application No. PCT/JP2016/000729, filed on Feb. 12, 2016.

(30) Foreign Application Priority Data

Feb. 12, 2015  (JP) .................................. 2015-025300

(51) Int. Cl.
  *A61K 9/06* (2006.01)
  *A61K 47/36* (2006.01)
  *A61K 47/26* (2006.01)

(52) U.S. Cl.
  CPC ............... *A61K 9/06* (2013.01); *A61K 47/26* (2013.01); *A61K 47/36* (2013.01)

(58) Field of Classification Search
  CPC ........................................................ A61K 9/06
  USPC ........................................................ 514/779
  See application file for complete search history.

(56) References Cited

U.S. PATENT DOCUMENTS

| | | | | |
|---|---|---|---|---|
| 2,673,157 | A * | 3/1954 | Shepherd | A23L 29/231 426/577 |
| 6,277,395 | B1 | 8/2001 | Fukui et al. | |
| 6,521,257 | B1 * | 2/2003 | Taniguchi | A61K 9/0056 424/434 |
| 2007/0231367 | A1 * | 10/2007 | Fukui | A23L 2/52 424/439 |

FOREIGN PATENT DOCUMENTS

| | | |
|---|---|---|
| EP | 2524687 A | 11/2012 |
| JP | S53-28087 A | 3/1978 |
| JP | 2000-325041 A | 11/2000 |
| JP | 3257983 B | 2/2002 |
| JP | 2002-218917 A | 8/2002 |
| JP | 2003-192573 A | 7/2003 |
| JP | 2004-043333 A | 2/2004 |
| JP | 2004-97114 A | 4/2004 |
| JP | 2004-173678 A | 6/2004 |
| JP | 2010-088422 A | 4/2010 |
| JP | 4647493 B | 3/2011 |
| WO | 98/58654 A | 12/1998 |
| WO | 2005/025622 A | 3/2005 |
| WO | 2009/098520 A | 8/2009 |
| WO | 2010/113325 A | 10/2010 |

OTHER PUBLICATIONS

International Search Report for PCT/JP2016/000729 dated May 10, 2016.
PCT written opinion dated May 10, 2016.
Japanese decision to grant a patent dated Apr. 4, 2017.
The extended European search report dated Jan. 30, 2018.
Notification of grounds for revocation in Japan dated Jan. 31, 2018.

* cited by examiner

*Primary Examiner* — Melenie L Gordon
*Assistant Examiner* — Taina D Matos Negron
(74) *Attorney, Agent, or Firm* — Yokoi & Co., U.S.A.; Toshiyuki Yokoi

(57) ABSTRACT

Provided is a jelly for assisting in taking a drug that reduces a possibility of aspiration and makes it possible to deliver a drug efficiently to the digestive tract without remaining in the throat. Contained are a gelling agent including LM pectin, agar, and other thickening polysaccharide and a gelling promoter to gel and is taken mixed with the drug when taking the drug; LM pectin is contained 1-3 wt % relative to the jelly for assisting in taking the drug; the properties at 20±2° C. of a jelly produced by chopping the jelly for assisting in taking the drug are a hardness of 2000-6000 N/m$^2$, adhesiveness of 200-500 J/m$^3$, and cohesiveness of 0.2-0.6; and the water separation from the jelly 10 minutes after chopping the jelly for assisting in taking the drug is 3 wt % or less relative to the jelly for assisting in taking the drug.

2 Claims, No Drawings

JELLY FOR ASSISTING IN TAKING DRUG

CROSS-REFERENCES TO RELATED APPLICATIONS

This application claims the benefit of priority and is a Continuation application of the prior International Patent Application No. PCT/JP2016/000729, with an international filing date of Feb. 12, 2016, which designated the United States, and is related to the Japanese Patent Application No. 2015-025300 filed Feb. 12, 2015, the entire disclosures of all applications are expressly incorporated by reference in their entirety herein.

BACKGROUND OF THE INVENTION

1. Field of the Invention

This invention relates to a jelly for assisting in taking a drug.

2. Description of Related Art

With the advent of an aging society in recent years, there are an increasing number of patients who are difficult to swallow in elderly people, cerebrovascular disorder patients, children and others. These who have difficulty in swallowing are not easy to take drug, so it cannot be swallowed sufficiently to remain in the mouth or be clogged in the throat, and there are cases where it is not possible to obtain the intended therapeutic effect. For those who have difficulty in swallowing, swallowing aids and the like have been variously studied and commercialized.

For those who have difficulty in swallowing, generally it is also a big problem to cause aspiration. If you aspirate food or moisture, you may develop aspiration pneumonia etc. by those entering bronchi/lung. A swallowing aid or the like which is used for taking a drug may sometimes leach out moisture in the oral cavity and be aspirated through the throat.

Compositions for assisting in taking a drug are described in Patent Documents 1 and 2.

Patent Document 1 describes a swallowing assist drink for a drug. In Example 1, a formulation prescription containing agar, locust bean gum, pectin, carrageenan, xanthan gum respectively in an amount of 0.01 to 0.2 parts by weight with respect to the total amount of 100 parts by weight is prepared, and its jelly strength is described as 46.6 g/cm². However, no mention is made at all about water separation, adhesiveness, cohesiveness etc.

Patent Document 2 describes that a swallowing aid that is characterized by forming of using jelly granules can freely wrap drugs of various dosage forms into a desired size shape and it can be swallowed extremely smoothly. Examples include those using xanthan gum and locust bean gum (1:1), those using sodium alginate and Konjac jelly, and those using sodium alginate and CMCNa. It was stated that the jelly of Example 1 had a jelly strength as very hard as 80,000 N/m² before being sieved to be granulated, and the jelly granules containing the granule agent inside became roughly spherical masses, and the granule agent did not flow out. As described above, since the jelly granule of Patent Document 2 is extremely hard and a mass, it is still not be easy to swallow for persons who have difficulty in swallowing.

Regarding foods for people with difficulty in swallowing, a notification (Ministry of Health, Labor and Welfare "Regarding the permission to display special-purpose foods") (No. 0212001 of the Department of Food Safety dated Feb. 12, 2009) has been issued. In this notification, the conventional expression for the older persons was changed to the expression for people with difficulty in swallowing as a special use, and the standards of permission criteria I, II and III are described to "permission criteria for display as a food for people with difficulty in swallowing" as follows.

TABLE 1

| standard ※1 | permission criteria I ※2 | permission criteria II ※3 | permission criteria III ※4 |
|---|---|---|---|
| Hardness (Resistance when compressed at a constant speed) (N/m²) | $2.5 \times 10^3 \sim 1 \times 10^4$ | $1 \times 10^3 \sim 1.5 \times 10^4$ | $3 \times 10^3 \sim 2 \times 10^4$ |
| Adhesiveness (J/m³) | Less than $4 \times 10^2$ | Less than $1 \times 10^3$ | Less than $1.5 \times 10^3$ |
| Cohesiveness | 0.2~0.6 | 0.2~0.9 | — |

※1 It shall be within the standard criteria under any conditions of normal temperature and a temperature as a guide for eating.
※2 Homogeneous (eg, jelly-like food)
※3 Homogeneous (eg, foods such as jelly-like or mousse-shaped food) However, excluding those that satisfy permission criteria I.
※4 Including heterogeneous items (eg, foods such as cohesive rice porridge, soft pasty or jelly) However, excluding those that satisfy permission criteria I or permission criteria II.

Based on this notification, it is generally thought that the one that meets the above permission criteria I is most preferable as a food for people with difficulty in swallowing. However, the "permission criteria for display as a food for people with difficulty in swallowing" does not describe at all about assisting in taking a drug and a mode of using by chopping foods for people with difficulty in swallowing. In addition, the above permission criteria does not include criteria for water separation.

Non-patent document 1 describes the answer to the question "Q11. What are the points to be kept in mind when letting eat jelly or crushed jelly?" as follows.

When eating solids, those are chewed, a mass of food is crushed once and then reformed into a bolus and sent to the throat. Similarly, a mass of jelly is put on a spoon and sent to the mouth, then chewing occurs. When a bolus cannot be formed, it is easy to aspirate as it is separated in the oral cavity, so the "method of drinking whole" is recommended. Also, in order not to crush the jelly, "slicing method" is also used to scoop the jelly flatly by a spoon and let drink whole. When crushing the jelly, if the cohesiveness is low, it remains disaggregated in the oral cavity, causing aspiration, and in general, as water is separated, it causes aspiration due to the separated moisture.

In addition, Non-Patent Document 1 does not describe at all about assisting in taking a drug and a mode of using by chopping foods for people with difficulty in swallowing.

Patent Document 3 describes a jelly for swallowing or the like having a cohesion with moderate hardness, less water separation, reduced adhesiveness. However, since the hardness of the jelly is as low as 600 to 2000 N/m², it does not satisfy the "permission criteria I for display as a food for people with difficulty in swallowing", which is not enough. Regarding water separation, it is not evaluated by a quantitative numerical value in the examples but is only sensuously evaluated, and it is unknown how much it was. Furthermore, Patent Document 3 does not describe at all about assisting in taking a drug and a mode of using by chopping foods for people with difficulty in swallowing.

Patent document 1: Japanese Patent No. 3257983
Patent document 2: JP 2004-43333 A
Patent document 3: JP 2010-88422 A
Non Patent document 1: Nutrition Care 2014 Spring Extra issue, page 66, Medica Publishing

BRIEF SUMMARY OF THE INVENTION

As described above, as a composition for assisting in taking a drug, an appropriate composition has not been obtained for those who have difficulty in swallowing, taking water separation into consideration.

If the water separation of the composition for assisting in taking a drug is high, it can cause aspiration by moisture that separates. Usually, chewing occurs unconsciously in the oral cavity, so if the same composition is chewed, moisture will be further separated and more aspiration will occur. If the same composition does not agglomerate in the oral cavity but remains separated, aspiration by the separated composition may occur. In addition, the method of drinking whole to drink same composition with a drug without chewing is not so easy for those who have difficulty in swallowing.

There, an object of the present invention is to solve the above problems, and it is the object of the present invention to provide a jelly for assisting in taking a drug, which is taken mixed with the drug when taking the drug, and can deliver the drug to a digestive organ easily and efficiently without putting a burden on drug recipients, and can keep the possibility of aspiration due to the water separation or the disaggregated composition low.

The present inventors considered that it is an optimal method to wrap a drug with chopped jelly in order to efficiently deliver the drug to the gastrointestinal tract without leaving the drug in the throat.

Hardness, adhesiveness, cohesiveness and water separation in chopped state were measured for three commercial products (commercial products A to C) marketed at present as swallowing aid jelly in Japan (See test example 1 described later). As a result, for both of the three commercial products, the hardness was 1000 N/m$^2$ or less, the adhesiveness was 80 J/m$^3$ or less, and the cohesiveness was 0.6 or more. Therefore, the commercial products A to C do not conform to the permission criteria I of "permission criteria for display as a food for those who have difficulty in swallowing" in a chopped state, barely complying with permission criteria III, it seemed that the effect is not high for swallowing aid in taking a drug. Also the water separation of the commercial products A to C was 5 wt %, 1.3 wt %, and 0 wt %, respectively. In the commercial product A, the water separation rate in the chopped jelly cannot be said as sufficiently low and it seems that the possibility of aspiration remains.

Therefore, in order to solve the above problems concerning the physical properties of the chopped jelly, it was thought that it is necessary to extremely reduce the water separation so as to reduce the possibility of aspiration to a low level, to increase the cohesiveness so that the jelly does not fall apart, to adjust the adhesiveness to a moderate range so that the jelly does not adhere to throat and esophagus, but stably wrap the drug, and to adjust to moderate hardness so that the jelly moves without clogging in throat and esophagus.

According to the above object, as a result of intensive studies by repeating trial and error with respect to a jelly for assisting in taking a drug, the present inventors found that products which combine low methoxyl pectin (LM pectin) as a main component with other gelling agent surprisingly can solve the above problem, and has almost no water separation, has high cohesiveness, has adequate adhesiveness and hardness, and can deliver the drug efficiently to the digestive tract without leaving the drug in throat or esophagus. And the present inventors completed the present invention. That is, the present invention is as follows.

[1] A jelly for assisting in taking a drug, comprising a gelling agent containing LM pectin, agar and other thickening polysaccharides, and a gelling promoter to gel and is taken mixed with the drug when taking the drug, wherein, LM pectin is contained 1 to 3 wt % relative to the jelly for assisting in taking the drug, physical properties at 20±2° C. of the jelly produced by chopping the jelly for assisting in taking the drug are hardness of 2000 to 6000 N/m$^2$, adhesiveness of 200 to 500 J/m$^3$, cohesiveness of 0.2 to 0.6, Water separation from the jelly 10 minutes after chopping the jelly for assisting in taking the drug is 3 wt % or less relative to the jelly for assisting in taking the drug.

(The jelly for assisting in taking the drug described in [1] satisfies the permission criteria II of display as food for those who have difficulty in swallowing with a margin, and has a sufficiently small amount of water separation.)

[2] The jelly for assisting in taking the drug described in [1], wherein,

LM pectin is contained 1.2 to 2.2 wt % relative to the jelly for assisting in taking the drug, physical properties at 20±2° C. of the jelly produced by chopping the jelly for assisting in taking the drug are hardness of 2500 to 6000 N/m$^2$, adhesiveness of 200 to 400 J/m$^3$, cohesiveness of 0.2 to 0.6, Water separation from the jelly 10 minutes after chopping the jelly for assisting in taking the drug is 1 wt % or less relative to the jelly for assisting in taking the drug.

(The jelly for assisting in taking the drug described in [2] satisfies the permission criteria I for display as a food for those who have difficulty in swallowing, and has extremely small amount of water separation. Even those who have difficulty in swallowing can take the drug with no fear of accidental swallowing.)

[3] The jelly for assisting in taking the drug described in [1] or [2], wherein the agar is contained 0.1 to 0.5 wt % and the other thickening polysaccharide is contained 0.1 to 1 wt %, relative to the jelly for assisting in taking the drug.

[4] The jelly for assisting in taking the drug described in any one of [1] to [3], wherein the other thickening polysaccharide is at least one kind of thickening polysaccharide selected from locust bean gum, xanthan gum, arabic gum, carrageenan, gellan gum, tara gum, guar gum, alginic acid, alginate, acacia gum and tamarind gum.

[5] The jelly for assisting in taking the drug described in any one of [1] to [4], further comprising an organic acid and/or an organic acid salt and having a pH of 3 or more and less than 4.

[6] The jelly for assisting in taking the drug described in [5], further comprising a sweetener.

[7] The jelly described in [6],
wherein the sweetener is a sugar alcohol among sugar-based sweetener sugar-based sweetener.

[8] The jelly described in [7], wherein the sugar alcohol is at least one kind of sugar alcohol selected from maltitol, xylitol and sorbitol.

Since the jelly for assisting in taking the drug of the present invention is used for taking drug mixed with the drug when taking the drug after chopping a gelled product, the water separation, hardness, adhesiveness and cohesiveness suitable for taking drug are measured in the jelly produced by gelling and chopping the jelly for assisting in taking the drug of the present invention. The jelly for assisting in taking the drug of the present invention has extremely small amount of water separation even when chopped. When measured by endoscopic examination, almost no moisture leaked into the throat even when chewing the jelly for assisting in taking the drug of the present invention in the oral cavity. In this way, since there is almost no moisture due to water separation and moisture generated by chewing unconsciously in the oral cavity, the risk of aspiration due to moisture is extremely small. In addition, the jelly for assisting in taking the drug of the present invention has high cohesiveness even when chopped. Therefore, the jelly for assisting in taking the drug does not become disaggregated in the oral cavity, and the risk of aspirating the jelly is small. Furthermore, since the jelly for assisting in taking the drug of the present invention has moderate adhesiveness even when chopped, drugs to be taken is wrapped in the jelly for assisting in taking the drug due to its adhesion, while throat and esophagus are not attached. In addition, since the jelly for assisting in taking the drug of the present invention has moderate hardness even when chopped, it passes through the throat and the esophagus without clogging in the throat and the esophagus, is delivered to the digestive tract.

As described above, according to the jelly for assisting in taking the drug of the present invention, since in the state where the jelly used for taking drug mixed with the drug when taking the drug is chopped, water separation is small, the jelly has high cohesiveness, moderate adhesiveness and moderate hardness to satisfy the permission criteria I or II of display as food for those who have difficulty in swallowing, there is no need to use a method to give a mental and physical pain like the method of drinking whole, and the possibility of aspiration is low, the drugs can be delivered to the digestive tract efficiently without remaining in the throat.

DETAILED DESCRIPTION OF THE INVENTION

1. Jelly for Assisting in Taking Drugs

The "jelly for assisting in taking drug" of the present invention includes a gelling agent containing LM pectin, agar and other thickening polysaccharides, and a gelling promoter.

As the "LM pectin", anything can be used as long as it can be gelled in the presence of a gelling promoter such as calcium ion. For example, any of acid treatment type and alkali treatment type in the deesterification method can be used, but acid treatment type is preferable. Preferred examples of LM pectin include those having an esterification degree of 26 to 34% and an amidation degree of 15 to 22%, more preferably those having an esterification degree of 28 to 34% and an amidation degree of 15 to 20%, and even more preferably those having an esterification degree of 28 to 33% and an amidation degree of 15 to 22%.

LM pectin is used as a main component for making the jelly for assisting in taking drugs of the present invention to have a desired hardness. In addition, by using LM pectin, it is possible to improve adhesiveness and suppress water separation. The content of LM pectin is 1 to 3 wt % relative to the jelly for assisting in taking drugs of the present invention. If it is less than 1 wt %, sufficient hardness cannot be obtained and water separation cannot be suppressed. On the other hand, when it exceeds 3 wt %, the adhesiveness becomes too large and it becomes unsuitable as the jelly for assisting in taking the drug. Preferred content are 1.1 to 2.5 wt %, more preferably 1.2 to 2.2 wt %, and even more preferably 1.3 to 2.1 wt %.

As the "agar", ordinary commercially available agar and the like are suitably used. Agar is added to increase the hardness of the jelly for assisting in taking the drug and to make the same jelly easy to be chopped. The content of agar is preferably 0.1 to 0.5 wt % relative to the jelly for assisting in taking the drug of the present invention. This is because when the content is 0.1 wt % or more, the above-mentioned effect is sufficiently obtained, and if it is contained in an amount of more than 0.5 wt %, there is a case that the water separation rate becomes large. It is more preferably 0.2 to 0.4 wt %, even more preferably 0.25 to 0.35 wt %.

The "other thickening polysaccharides" include for example locust bean gum, xanthan gum, Arabic gum, carrageenan, Gellan gum, Tara gum, guar gum, Alginic acid, alginate, acacia gum, tamarind gum and these mixtures etc. Preferred examples include mixtures of locust bean gum and xanthan gum. When a mixture of two components is used, it can be mixed at a suitable weight ratio, for example 1:9 to 9:1, preferably 3:7 to 7:3.

Other thickening polysaccharides are used to reduce water separation and improve hardness and adhesiveness. The content of other thickening polysaccharide is preferably 0.1 to 1 wt % relative to the jelly for assisting in taking the drug of the present invention. This is because when the content is 0.1 wt % or more, the above-mentioned effects are sufficiently obtained, and when it is contained in an amount exceeding 1 wt %, the hardness and adhesiveness may become too high in some cases. It is more preferably 0.2 to 0.7 wt %, even more preferably 0.3 to 0.5 wt %.

As the "gelling promoter", anything that provides calcium ions can be used. For example, calcium lactate, tricalcium phosphate, calcium chloride, calcium gluconate, calcium hydrogen phosphate, calcium dihydrogen phosphate, calcium trihydrogen phosphate, calcium carbonate, calcium sulfate and the like can be mentioned, and these mixtures can be used. Calcium lactate is mentioned as a preferred gelling promoter.

Gelling promoter is used to gel LM pectin. There, an amount suitable for gelation to a desired state is used. The content of the gelling promoter is preferably 0.05 to 0.5 wt % relative to LM pectin if it is represented by the case where calcium lactate is used. This is because gelling progresses at an appropriate rate at 0.05 wt % or more, and even if it is contained in an amount of more than 0.5 wt %, the gelling promoting effect is saturated. It is more preferably 0.1 to 0.3 wt %, even more preferably 0.15 to 0.25 wt %.

The jelly for assisting in taking the drug of the present invention may contain as other ingredients, such as a coloring agent, a sweetener, a perfume, a stabilizer, a preservative, alcohols, natural fruit juice, an organic acid, an organic acid salt and the like. Examples of the sweetener include sugar, oligosaccharide, maltitol, erythritol, sorbitol, xylitol, aspartame (registered trademark), acesulfame potassium, sucralose, stevia and the like. As the organic acid and/or the organic acid salt, as long as it can adjust the pH of the jelly for assisting in taking the drug to 3 or more and less than 4, preferably 3.3 to 3.9, more preferably 3.5 to 3.8 and it can be edible, it can be anything. Preferred organic acids include, for example, citric acid, tartaric acid, malic acid, succinic acid, ascorbic acid, glucuronic acid, benzoic acid and the like, and more preferred is citric acid. Examples of the organic acid salt include alkali salts (for example, sodium salt, potassium salt, etc.) of these organic acids.

The jelly for assisting in taking the drug of the present invention is used for taking drugs after chopping. Therefore, "hardness", "adhesiveness" and "cohesiveness" suitable for taking the drug can be confirmed by measuring at 20±2° C. in a jelly produced by chopping the jelly for assisting in taking the drug of the present invention. "Hardness", "adhesiveness" and "cohesiveness", as described in the examples described later, can be measured according to the measurement method described in the notification as "Regarding the permission to display special-purpose foods") (No. 0212001 of the Department of Food Safety dated Feb. 12, 2009).

"Hardness" at 20±2° C. of the jelly produced by chopping the jelly for assisting in taking the drug of the present invention is 2000 to 6000 N/m$^2$, preferably 2500 to 6000 N/m$^2$, and more preferably 2700 to 5000 N/m$^2$.

"Adhesiveness" at 20±2° C. of the jelly produced by chopping the jelly for assisting in taking the drug of the present invention is 200 to 500 J/m$^3$, preferably 200 to 400 J/m$^3$, and more preferably 230 to 350 J/m$^3$.

"Cohesiveness" at 20±2° C. of the jelly produced by chopping the jelly for assisting in taking the drug of the present invention is 0.2 to 0.6, preferably 0.3 to 0.5.

"Hardness", "adhesiveness" and "cohesiveness" at 20±2° C. of the jelly produced by chopping the jelly for assisting in taking the drug of the present invention can be easily adjusted by appropriately increasing or decreasing the content of LM pectin, agar and other thickening polysaccharide within the above range.

"Water separation" of the jelly produced by chopping the jelly for assisting in taking the drug of the present invention is 3 wt % or less relative to the jelly for assisting in taking the drug of the present invention 10 minutes after chopping. The water separation is preferably 2 wt % or less, more preferably 1 wt % or less, even more preferably 0.5 wt % or less, particularly preferably 0.2 wt % or less. Chopping is performed by, for example, the method used in the test examples described later. The reason for using the water separation after 10 minutes from chopping as a reference is because it is usually within about 10 minutes that the recipient chops the jelly, for example by pushing out from a pack container containing the jelly for assisting in taking the drug inside, and then takes the jelly mixed with a drug.

2. Method for Producing Jelly for Assisting in Taking Drug

The jelly for assisting in taking the drug of the present invention can be produced, for example, by adding an organic acid and/or an organic acid salt to an aqueous solution of gelling agent containing LM pectin, agar and other thickening polysaccharides, gelling promoter, and optional components added as necessary, to adjust the pH of the aqueous solution to 3 or more and less than 4, and gelling the solution.

In order to prepare an aqueous solution of a gelling agent containing LM pectin, agar and other thickening polysaccharides, a gelling promoter, and optional components to added as necessary, for example, it is preferable to dissolve from a substance having a high melting temperature sequentially, to suppress decomposition of substances. For example, in the case of dissolving LM pectin, agar, locust bean gum and xanthan gum in heated water, it can be dissolved in water heated in the order of agar, locust bean gum, xanthan gum, LM pectin. In order to promote dissolution, it is also preferable to previously mix well the LM pectin, the gelling agent and the thickening polysaccharide with the saccharide and to dissolve them as a mixture in water. It is preferable to fully defoam after dissolving in heated water. Thereafter, an aqueous solution of an organic acid and/or an organic acid salt is added to the obtained aqueous solution to adjust the pH to 3 or more and less than 4, preferably 3.3 to 3.9, more preferably 3.5 to 3.8. Thereafter, for example, by adding the obtained jelly solution to a container, standing still it in a cold place, or cooling down it to room temperature and then standing still in a refrigerator, it is possible to manufacture the jelly for assisting in taking the drug of the present invention.

3. Use of Jelly to Assisting in Taking Drug

A jelly for assisting in taking the drug of the present invention is used for taking drugs after chopping. As a method of chopping, for example, the jelly for assisting in taking the drug can be placed in a perforated chopper having a fixed diameter, and it can be chopped by pushing out with a pressure plate. In addition, a part of a pack container containing the jelly for assisting in taking the drug inside is cut with a scissors and a hole is opened so as to have an appropriate slit width, then, by applying pressure to the pack container and pushing out internal the jelly for assisting in taking the drug to the outside, chopping can also be performed. As the diameter of the hole or the slit width when chopping is performed, for example, about 4 to 15 mm is mentioned, preferably about 7 to 13 mm.

Mix the chopped jelly for assisting in taking the drug with one or more drugs and take it. In addition, one or more drugs can also be taken using a split body.

EXAMPLE

Hereinafter, the present invention will be described in more detail with reference to examples and test examples, but the present invention is not limited to these examples at all.

This test example was measured using the following method.

A. Method of Making Chopped Jelly

Scrape off 200 g of the jelly in the container with a spatula and fill it into a 2 mm φ perforated chopper. Push out with a pressure plate and receive on a stainless steel cup. Scrape off from a stainless steel cup with a spatula and store in a storage container and store in a temperature keeping room at 20±2° C. for about 30 minutes.

B. Method for Measuring Physical Properties (Hardness, Adhesiveness, Cohesiveness) of Chopped Jelly According to the "Test method of food for people with difficulty in swallowing" of the Ministry of Health, Labor and Welfare's Notice "Regarding the permission to display special purpose foods" (No. 0212001 of the Department of Food Safety), the physical properties (hardness, adhesiveness, cohesiveness) are measured. Concrete measurement methods are as follows.

The chopped jelly made in A. above is scooped up with spatula and is packed in two containers with a diameter of 40 mm and a height of 15 mm more than the height of 15 mm. Pull out the air in the chopped jelly by tapping the bottom of the container ten times on the top board of the desk etc. Cut off those that protrude from the upper edge of the container with a cutter or the like, put the container in a sealed container, and store in a temperature keeping room of 20° C. for about 30 minutes. One of the two containers is dedicated to temperature measurement and when the jelly of the other container is measured, the jelly temperature is measured to confirm that it is 20° C.

The chopped jelly in the other container is measured by using an apparatus capable of measuring compressive stress of a substance by linear motion, using a plastic plunger having a diameter of 20 mm and a height of 8 mm, compress measurement are done twice with a compression speed 10 mm/sec and a clearance 5 mm. Measurement items are hardness, adhesiveness, cohesiveness, and weight of jelly, and it is confirmed that the jelly temperature is 20° C. after the measurement.

<Measuring Apparatus>

Rheoner II Creep Meter RE2-33005C made by Yamaden (Desk recorder: RE-3305-3 N, Analog output remodeling: RE 2-OP 20 C)

Plunger: L50+L17+No. 56

<Measured Value>

Set the Creep Meter as follows.

The thickness of the jelly sample is fixed at 15 mm, the jelly sample is not contacted until the measurement and the automatic thickness measurement is not carried out. The distortion factor is fixed at 66.7%. The measurement start sensitivity setting is 0.02 N/3 times. A2 measurement start sensitivity is 0.02 N/2 times.

C. Method for Measuring Water Separation

Place a 60 mm diameter glass funnel on a funnel base. A polyethylene mesh (20 mesh standard product) cut according to the glass funnel and welded is placed. Place a measuring device put on an electronic balance under a dropping port of the funnel.

A 25 g of the chopped jelly made in above A. is placed on the polyethylene mesh and the water weight dropped every 2 minutes to 10 minutes is recorded for 30 minutes. Calculate the water separation after 10 minutes from the chopping by weight % relative to the jelly for assisting in taking the drug.

Experiment 1. Preparation of Jelly for Assisting in Taking Drug (1)

1 kg of a jelly solution was prepared by mixing the ingredients shown in Table 2 in the amounts shown in Table 2, and by gelling the jelly solution, the jellies for assisting in taking the drugs of Examples 1 to 6, and Comparative Examples 1 and 2 were prepared.

jelly solution was filled in a predetermined container at about 60° C. and stored at about 5° C. to obtain a jelly for assisting in taking drug.

Test Example 1. Physical Properties of Chopped State of Commercial Jellies for Swallowing Aid For three commercial products (commercial products A to C) that are currently marketed as swallowing aid jelly in Japan, hardness, adhesiveness, cohesiveness and water separation in chopped state were measured. The results are shown in Table 3.

TABLE 3

|  | commercial product A | commercial product B | commercial product C |
| --- | --- | --- | --- |
| Hardness (N/m$^2$) | 664 | 398 | 969 |
| Adhesiveness (J/m$^3$) | 80 | 49 | 80 |
| Cohesiveness | 0.61 | 0.69 | 0.77 |
| Water separation after 10 minutes (weight %) | 5 | 1.3 | 0 |

For all the three commercial products, the hardness was 1000 N/m$^2$ or less, the adhesiveness was 80 J/m$^3$ or less, and the cohesiveness was 0.6 or more. Based on these measured values, the three commercial products do not conform to the permission criteria I of the "permission criteria for display as a food for those who have difficulty in swallowing", barely conforming to the permission criteria III, and it seems that the effect for swallowing assistance is not high. Furthermore, with respect to water separation of the three commercial products, the commercial products A to C were 5 wt %, 1.3 wt % and 0 wt % respectively, it cannot be said that water separation in chopped state of commercial product A was low.

TABLE 2 unit: weight %

| | gelling agent | | other thickening polysaccharide | | gelling promoter | organic acid | | | |
| --- | --- | --- | --- | --- | --- | --- | --- | --- | --- |
| No | LM pectin | agar | locust bean gum | xanthan gum | calcium lactate | citric acid | sweetener | water | total |
| comparative example 1 | 0.52 | 0.3 | 0.2 | 0.2 | 0.24 | 0.37 | 12.2 | remaining | 100 |
| comparative example 2 | 0.78 | 0.3 | 0.2 | 0.2 | 0.24 | 0.37 | 12.2 | remaining | 100 |
| example 1 | 1.04 | 0.3 | 0.2 | 0.2 | 0.24 | 0.37 | 12.2 | remaining | 100 |
| example 2 | 1.30 | 0.3 | 0.2 | 0.2 | 0.24 | 0.37 | 12.2 | remaining | 100 |
| example 3 | 1.56 | 0.3 | 0.2 | 0.2 | 0.24 | 0.37 | 12.2 | remaining | 100 |
| example 4 | 1.82 | 0.3 | 0.2 | 0.2 | 0.24 | 0.37 | 12.2 | remaining | 100 |
| example 5 | 2.08 | 0.3 | 0.2 | 0.2 | 0.24 | 0.37 | 12.2 | remaining | 100 |
| example 6 | 2.34 | 0.3 | 0.2 | 0.2 | 0.24 | 0.37 | 12.2 | remaining | 100 | sweetener: granulated sugar, reduced maltose syrup and xylitol

As a concrete preparation method, water was added to a reaction vessel, heated to 60 to 90° C., and the ingredients shown in Table 2 were sequentially added and dissolved. At that time, LM pectin, locust bean gum and xanthan gum were mixed with part of the sweetener and then added to the aqueous solution. Thereafter, citric acid was added to adjust the pH of the aqueous solution to about 3.7, followed with degassing to prepare 1 kg of the jelly solution. The obtained From the above, it understood that the three commercial products are not sufficient for assisting in taking drug.

Test Example 2. Physical Properties of the Jelly Prepared in Experiment 1

For the jelly obtained in Experiment 1, hardness, adhesiveness, cohesiveness and water separation in chopped state were measured. The results are shown in Table 4.

TABLE 4

|  | comparative example 1 | comparative example 2 | example 1 | example 2 | example 3 | example 4 | example 5 | example 6 |
|---|---|---|---|---|---|---|---|---|
| Hardness (N/m$^2$) | 1137 | 1564 | 2069 | 2987 | 3574 | 3651 | 4984 | 5575 |
| Adhesiveness (J/m$^3$) | 163 | 195 | 242 | 244 | 323 | 305 | 389 | 449 |
| Cohesiveness | 0.56 | 0.52 | 0.51 | 0.46 | 0.47 | 0.46 | 0.44 | 0.48 |
| Water separation after 10 minutes (weight %) | 8.4 | 5.6 | 1.9 | 0.1 | 0.0 | 0.0 | 0.0 | 0.0 |

The jellies of Examples 1 to 6 had hardness of 2000 to 6000 N/m$^2$, adhesiveness of 200 to 500 J/m$^3$, cohesiveness of 0.2 to 0.6, and water separation after 10 minutes was small. Especially, the jellies of Examples 2 to 5 had hardness of 2500 to 6000 N/m$^2$, adhesiveness of 200 to 400 J/m$^3$, cohesiveness of 0.2 to 0.6, and water separation after 10 minutes was almost none. Therefore, the jellies of Examples 1 to 6 are suitable for assisting in taking drugs, and the jellies of Examples 2 to 5 are further suitable for assisting in taking drugs.

On the other hand, the jellies of Comparative Examples 1 and 2 had hardness of less than 2000 N/m$^2$, adhesiveness less than 200 J/m$^3$, and considerable water separation.

Experiment 2. Preparation of Jelly for Assisting in Taking Drug (2)

1 kg of a jelly solution was prepared by mixing the ingredients shown in Table 5 in the amounts shown in Table 5, and by gelling the jelly solution, the jellies for assisting in taking drugs of Examples 7 to 15 and Comparative Examples 3 to 5 were prepared. The concrete preparation method is the same as in Experiment 1. Examples 7 to 9, 12 and 13 are the case where the weight ratio of locust bean gum to xanthan gum was changed to 1, 1.5, 3, 1/1.5, 1/3 while keeping the total amount of locust bean gum and xanthan gum at 0.4 wt %. Examples 10 and 11 are the case where the addition amount of locust bean gum was changed to 0.4 wt % and 0.2 wt % without adding xanthan gum, whereas comparative examples 3 and 4 are the case where the addition amount of xanthan gum was changed to 0.4 wt % and 0.2 wt % without adding locust bean gum. Comparative Example 5 is the case where locust bean gum and xanthan gum were not added together. The amounts of ingredients other than locust bean gum and xanthan gum correspond to Example 2 of Experiment 1. Example 14 is the case where instead of no adding locust bean gum and xanthan gum together, the amount of pectin was increased by 0.4 wt % to 1.7 wt %. Example 15 is the case where agar is not added. The sweetener is fixed in a mixture of granulated sugar (2.5 wt %), maltitol (4.5 wt %) and xylitol (5.2 wt %). In addition, maltitol is the same substance as reduced maltose syrup.

TABLE 5 unit: weight %

| | gelling agent | | | | gelling promoter | organic acid | | | |
|---|---|---|---|---|---|---|---|---|---|
| | | | other thickening polysaccharide | | | | | | |
| No | LM pectin | agar | locust bean gum | xanthan gum | calcium lactate | citric acid | sweetener | water | total |
| example 7 | 1.30 | 0.3 | 0.2 | 0.2 | 0.24 | 0.37 | 12.2 | remaining | 100 |
| example 8 | 1.30 | 0.3 | 0.24 | 0.16 | 0.24 | 0.37 | 12.2 | remaining | 100 |
| example 9 | 1.30 | 0.3 | 0.3 | 0.1 | 0.24 | 0.37 | 12.2 | remaining | 100 |
| example 10 | 1.30 | 0.3 | 0.4 | 0 | 0.24 | 0.37 | 12.2 | remaining | 100 |
| example 11 | 1.30 | 0.3 | 0.2 | 0 | 0.24 | 0.37 | 12.2 | remaining | 100 |
| example 12 | 1.30 | 0.3 | 0.16 | 0.24 | 0.24 | 0.37 | 12.2 | remaining | 100 |
| example 13 | 1.30 | 0.3 | 0.1 | 0.3 | 0.24 | 0.37 | 12.2 | remaining | 100 |
| comparative example 3 | 1.30 | 0.3 | 0 | 0.4 | 0.24 | 0.37 | 12.2 | remaining | 100 |
| comparative example 4 | 1.30 | 0.3 | 0 | 0.2 | 0.24 | 0.37 | 12.2 | remaining | 100 |
| comparative example 5 | 1.30 | 0.3 | 0 | 0 | 0.24 | 0.37 | 12.2 | remaining | 100 |
| example 14 | 1.70 | 0.3 | 0 | 0 | 0.24 | 0.37 | 12.2 | remaining | 100 |
| example 15 | 1.30 | 0 | 0.2 | 0.2 | 0.24 | 0.37 | 12.2 | remaining | 100 | sweetener: granulated sugar(2.5), reduced maltose syrup(4.5) and xylitol(5.2)

Test Example 3. Physical Properties of the Jelly Prepared in Experiment 2

For the jelly obtained in Experiment 2, hardness, adhesiveness, cohesiveness, water separation and PH in chopped state were measured. The results are shown in Table 6 and Table 7. Regarding water separation, both water separation after 10 minutes and water separation after 30 minutes were measured.

The jelly (Examples 7 to 9, 12, 13) in which the weight ratio of locust bean gum to xanthan gum was varied in the range of 3 to ⅓ had hardness of 2519 to 2878 N/m², adhesiveness of 246 to 287 J/m³, cohesiveness of 0.44 to 0.47, and pH of 3.57 to 3.68. The water separation is very small because a water separation 10 minutes is 0.1 wt % or less after and a water separation after 30 minutes is 2.2 wt % or less. Therefore, the jellies of Examples 7 to 9, 12 and 13 are suitable for assisting in taking drugs.

The jelly (Example 10) added with 0.4 wt % of locust bean gum without adding xanthan gum is good as it had hardness of 2742 N/m², cohesiveness of 0.48, pH of 3.67, water separation after 10 minutes of 0.0 wt % and water separation after 30 minutes of 0.8 wt %, but is easy to stick to the oral cavity and teeth, having adhesiveness of somewhat high at 368 J/m³. The jelly (Example 11) in which xanthan gum was not added and the addition amount of locust bean gum was reduced to 0.2 wt % had insufficient hardness with 2237 N/m², and had large water separation as the water separation after 10 minutes was 0.8 wt % and water separation after 30 minutes was 3.9 wt %, is easy to separate water.

The jelly (Comparative Example 3) added with 0.4 wt % of xanthan gum without adding locust bean gum has a small amount of water separation but a large deficiency at a hardness of 1360 N/m², and because it has a high cohesiveness of 0.79 and a strong elasticity, the resistance across the throat is great, and adhesiveness is high at 472 J/m³, so it tends to stick to the oral cavity and teeth. In the jelly (Comparative Example 4) in which the addition amount of xanthan gum was reduced to 0.2 wt %, the hardness further decreased, and the cohesiveness was as high as 0.74, so the resistance across the throat was great, and the adhesiveness was 357 J/m³, so the tendency that it tends to stick to the oral cavity and teeth is maintained.

The jelly (Comparative Example 5) without adding both locust bean gum and xanthan gum has a largely deficiency with a hardness of 1623 N/m², and a large water separation as 2.8 wt % of water separation after 10 minutes, 7.4 wt % of water separation after 30 minutes. The jelly (Example 14) in which the amount of pectin was increased to 1.7 wt % instead of no adding locust bean gum and xanthan gum together was a good result with regard to hardness, adhesiveness, cohesiveness, and water separation. However, both sweetness and sourness are strong results in evaluation of taste. The jelly without adding agar (Example 15) is good with respect to hardness, adhesiveness, and water separation, but the resistance across the throat becomes large because the cohesiveness is slightly high at 0.54.

TABLE 7

|  | comparative example 5 | example 14 | example 15 |
|---|---|---|---|
| Hardness (N/m²) | 1623 | 2883 | 2596 |
| Adhesiveness (J/m³) | 236 | 280 | 250 |
| Cohesiveness | 0.51 | 0.48 | 0.54 |
| Water separation after 10 minutes (weight %) | 2.8 | 0.0 | 0.0 |
| Water separation after 30 minutes (weight %) | 7.4 | 1.4 | 0.0 |
| PH | 3.65 | 3.68 | 3.68 |

Experiment 3. Preparation of Jelly for Assisting in Taking Drug (3)

In Experiments 1 and 2, the sweetener to be added was fixed in a mixture of granulated sugar, reduced maltose syrup (maltitol) and xylitol, but the type of sweetener was changed in Experiment 3. A jelly solution was prepared by mixing the ingredients shown in Table 8 in the amounts shown in Table 8, and by gelling the jelly solution, jellies for assisting in taking drug of Comparative Example 6 without adding sweetener and Example 16 to 25 with various sweeteners added were prepared. The concrete preparation method is the same as in Experiments 1 and 2. Maltitol, sorbitol, erythritol, xylitol used in Examples 17 to 21 belong to sugar alcohols among sugar-based sweeteners, and the stevia, aspartame (registered trademark), acesulfame potassium, Sucralose are non-carbohydrate sweeteners. In order to improve the preservability of jelly (pectin), 0.3 wt % of citric acid was added as a PH regulator to keep at less than PH 4, and in order to suppress the acidity of citric acid as an acidulant, a sweetener was used. The granulated sugar was well balanced between acidity and sweetness with the addition of 11 wt %. For other sweeteners, the amount added was adjusted so as to be as sweet as granulated sugar case depending on the degree of sweetness.

TABLE 6

|  | example 7 | example 8 | example 9 | example 10 | example 11 | example 12 | example 13 | comparative example 3 | comparative example 4 |
|---|---|---|---|---|---|---|---|---|---|
| Hardness (N/m²) | 2878 | 2683 | 2756 | 2742 | 2237 | 2573 | 2519 | 1360 | 1219 |
| Adhesiveness (J/m³) | 274 | 270 | 287 | 368 | 261 | 246 | 273 | 472 | 357 |
| Cohesiveness | 0.44 | 0.47 | 0.45 | 0.48 | 0.47 | 0.45 | 0.47 | 0.79 | 0.74 |
| Water separation after 10 minutes (weight %) | 0.0 | 0.0 | 0.1 | 0.0 | 0.8 | 0.0 | 0.0 | 0.0 | 0.0 |
| Water separation after 30 minutes (weight %) | 2.0 | 2.2 | 2.2 | 0.8 | 3.9 | 2.2 | 1.7 | 0.1 | 0.0 |
| PH | 3.57 | 3.67 | 3.67 | 3.67 | 3.67 | 3.68 | 3.67 | 3.68 | 3.67 |

TABLE 8 unit: weight %

|  |  | gelling agent | | | | | gelling promoter | organic acid | | |
|---|---|---|---|---|---|---|---|---|---|---|
|  |  |  |  | other thickening polysaccharide | | | | | | |
| No | sweetener | LM pectin | agar | locust bean gum | xanthan gum | | calcium lactate | citric acid | water | total |
| comparative example 6 | none | 1.30 | 0.3 | 0.2 | 0.2 | | 0.24 | 0.37 | remaining | 100 |
| example 16 | Granulated sugar 11 | 1.30 | 0.3 | 0.2 | 0.2 | | 0.24 | 0.37 | remaining | 100 |
| example 17 | Maltitol 12 | 1.30 | 0.3 | 0.2 | 0.2 | | 0.24 | 0.37 | remaining | 100 |
| example 18 | Sorbitol 18 | 1.30 | 0.3 | 0.2 | 0.2 | | 0.24 | 0.37 | remaining | 100 |
| example 19 | Erythritol 14 | 1.30 | 0.3 | 0.2 | 0.2 | | 0.24 | 0.37 | remaining | 100 |
| example 20 | Xylitol 11 | 1.30 | 0.3 | 0.2 | 0.2 | | 0.24 | 0.37 | remaining | 100 |
| example 21 | Granulated sugar 2.5 Maltitol 4.5 Xylitol 5.2 | 1.30 | 0.3 | 0.2 | 0.2 | | 0.24 | 0.37 | remaining | 100 |
| example 22 | Stevia 0.037 | 1.30 | 0.3 | 0.2 | 0.2 | | 0.24 | 0.37 | remaining | 100 |
| example 23 | Aspartame 0.055 | 1.30 | 0.3 | 0.2 | 0.2 | | 0.24 | 0.37 | remaining | 100 |
| example 24 | Acesulfame potassium 0.056 | 1.30 | 0.3 | 0.2 | 0.2 | | 0.24 | 0.37 | remaining | 100 |
| example 25 | Scuralose 0.019 | 1.30 | 0.3 | 0.2 | 0.2 | | 0.24 | 0.37 | remaining | 100 |

Test Example 4. Physical Properties of the Jelly Prepared in Experiment 3

For each jelly obtained in Experiment 3, hardness, adhesiveness, cohesiveness, water separation and PH in chopped state were measured. The results are shown in Table 9. Regarding water separation, both water separation after 10 minutes and water separation after 30 minutes were measured.

TABLE 9

|  | comparative example 6 | example 16 | example 17 | example 18 | example 19 | example 20 | example 21 | example 22 | example 23 | example 24 | example 25 |
|---|---|---|---|---|---|---|---|---|---|---|---|
| Hardness (N/m²) | 2343 | 2460 | 2938 | 3547 | 2824 | 2778 | 2878 | 2569 | 2628 | 2255 | 2274 |
| Adhesiveness (J/m³) | 244 | 281 | 284 | 346 | 300 | 275 | 274 | 263 | 263 | 242 | 249 |
| Cohesiveness | 0.47 | 0.47 | 0.46 | 0.46 | 0.44 | 0.45 | 0.44 | 0.44 | 0.46 | 0.47 | 0.47 |
| Water separation after 10 minutes (weight %) | 3.1 | 1.8 | 0.6 | 0.0 | 1.3 | 0.0 | 0.0 | 2.3 | 2.3 | 1.4 | 1.1 |
| Water separation after 30 minutes (weight %) | 7.0 | 5.7 | 3.7 | 0.0 | 5.4 | 0.5 | 2.0 | 6.1 | 6.7 | 5.2 | 3.9 |
| PH | 3.69 | 3.67 | 3.74 | 3.73 | 3.72 | 3.72 | 3.57 | 3.68 | 3.69 | 3.75 | 3.65 |

The jelly of Comparative Example 6 (sweetener not added) has a large water separation after 10 minutes as 3.1 wt %, and is not suitable for assisting in taking drugs. The jelly of Example 16 (granulated sugar) is harder and has greater adhesiveness than the jelly of Comparative Example 6, but has comparable cohesiveness and PH. With regard to water separation, the water separation after 10 minutes is slightly small as 1.8 wt %, and it can be used to assisting in taking drugs.

The jelly of Examples 17 to 21 (sugar alcohol) have hardness of 2778 to 3547 N/m², adhesiveness of 274 to 346 J/m³, cohesiveness of 0.44 to 0.46, PH of 3.57 to 3.74, in each range. The hardness is harder than that of the jelly of Comparative Example 6. Regarding water separation, the jelly of Example 17 (sweetener: maltitol), 18 (sweetener: sorbitol), 20 (sweetener: xylitol), and 21 (sweetener: mixture of granulated sugar and maltitol and xylitol) had small water separation after 10 minute as less than 1 wt %. Especially, the jelly of Examples 18, 20 and 21 had no water separation after 10 minutes, and the jelly of Examples 18 and 20 had also extremely low water separation after 30 minutes as 1 wt % or less. Therefore, by adding maltitol, xylitol and sorbitol, the hardness of the jelly with LM pectin compound increased and the great effect of decreasing water separation was confirmed. The jellies of Examples 17 to 21 are suitable for assisting in taking drugs, and the jellies of Examples 18 and 20 are further suitable for assisting in taking drugs.

The jellies of Examples 22 to 25 had hardness of 2255 to 2628 N/m², the effect of hardening the jelly is not large, the adhesiveness was 242 to 263 J/m³, the cohesiveness was 0.44 to 0.47, PH was in the range of 3.65 to 3.75. Regarding water separation, the water separation after 10 minutes exceeds 1 wt %, and although there is an effect of reducing the water separation, it is smaller than the jellies of Examples 17 to 21.

Experiment 4. Bolus Forming Property and Dispersibility in Water of Jelly

It is desirable that the jelly for assisting in taking drugs moves as a bolus with moderate flexibility as a capsule wrapping the drug from in the oral cavity and the throat to in the esophagus, and quickly disperses due to moisture in the stomach and releases the drug. There, for several kinds of jellies obtained in Experiments 2 and 3 and commercial product D of jelly, bolus forming property and dispersibility in water were measured. The results are shown in Table 10. Incidentally, the measurement values of the physical properties of commercial product D of jelly were hardness 700 $N/m^2$, adhesiveness 119.1 $J/m^3$, cohesiveness 0.54, water separation rate after 10 minutes 3.8 wt %, and PH 3.7.

Regarding bolus forming property, 10 g of the jelly sample was dropped down from a height of 50 cm, and the strength of the bolus formation was evaluated by the radius (diffusion radius) of the deformed and diffused sample. It is judged that the smaller the diffusion radius is, the stronger the bolus forming property is, and the larger the diffusion radius (mm), the weaker the bolus forming property.

Regarding the dispersibility in water, a rotor was placed in a conical beaker containing 300 mL of water, stirred with a stirrer at a rotation speed of 300 rpm, and 10 g of the jelly sample was dropped into the conical beaker and time (sec) to disperse the jelly sample to a mass of 3 mm or less was measured.

TABLE 10

|  |  | example 7 | comparative example 3 | comparative example 5 | example 15 | example 19 | commercial product D |
|---|---|---|---|---|---|---|---|
| Bolus formability | Diffusion radius (mm) | 3.5 | 25.2 | 34.3 | 24.8 | 28.2 | 39.5 |
| Dispersibility in water | Dispersion time (sec) | 7.1 | 5 minutes or more | 63.5 | 12.1 | 7.6 | 4 |

For Comparative Example 3, the stirring was continued for 5 minutes, but since the jelly block having the size of about azuki beans remained, the dispersion time was set to 5 minutes or more.

In Example 7 and Example 15 in which the physical property value corresponding to the permission criteria I of food display for those who have difficulty in swallowing, it could be confirmed that the bolus forming power was relatively strong and the dispersion time in water was relatively short.

As Comparative Example 5, Example 19, and Commercial Product D, those having large water separation had relatively weak bolus forming power. When the hardness was less than 2000 $N/m^2$ as in Comparative Example 5, the dispersion time in water was also longer.

Furthermore, as in Comparative Example 3, when the hardness is less than 2000 $N/m^2$, the cohesiveness exceeds 0.6 and the adhesiveness exceeds 400 $J/m^3$, the dispersion time in water was extremely longer.

It was confirmed that the jelly which is in the range of the physical property value close to the permission criteria I of food display for those who have difficulty in swallowing and has small water separation is a jelly having excellent bolus forming property and fast dispersion speed in water.

Experiment 5. Long Term Stability of Jelly

For the sample in which the jelly of the formulation of Example 7 described in Experiment 2 was sealed in a film with high barrier property, an evaluation test on long-term storability in the room was conducted and the following results were obtained. Incidentally, the film has a three-layer structure in which a PET layer having high barrier property is disposed on the outer side, a nylon layer with high moisture resistance is set as an intermediate layer, and a polyethylene layer is provided as a sealant layer on the inner side. The jelly was sandwiched between two sheets of film in which the polyethylene layers are opposed to each other, and the periphery was heat-sealed to prepare a sample.

The hardness, cohesiveness and adhesiveness of the sample after 23 months passed was within the range of about 10 to 7% change with respect to the initial value.

With regard to water separation, the water separation of the sample after 23 months passed was equivalent to the initial value.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

INDUSTRIAL APPLICABILITY

According to the present invention, a jelly for assisting in taking a drug, which is low in possibility of aspiration and can be efficiently delivered to the digestive device without remaining drug in throat and a method for producing the same, are provided.

What is claimed is:

1. A jelly for assisting in taking a drug comprising: a gelling promoter;
a sweetener wherein the sweetener is at least one sugar alcohol selected from the group consisting of maltitol, xylitol and sorbitol; and a gelling agent comprising
- (a) low methoxy pectin in an amount of 1.2 to 2.2 wt % based on the total amount of the jelly;
- (b) agar in an amount of 0.1 to 0.5 wt % based on the total amount of the jelly; and
- (c) an additional thickening polysaccharide selected from the group consisting of locust bean gum and xanthan gum in an amount of 0.1 to 1 wt % based on the total amount of the jelly and when present the locust bean gum is in an amount of at least 0.1 wt % based on the total amount of the jelly;

wherein the physical properties of the jelly at 20±2° C. after chopping are hardness is 2500 to 6000 N/m$^2$;

adhesiveness is 200 to 400 J/m$^3$;

cohesiveness is 0.2 to 0.6; and wherein the amount of water separated from the jelly in 10 minutes after chopping is 1 wt % or less based on the total amount of the jelly.

2. The jelly for assisting in taking the drug as defined in claim 1;

further comprising an organic acid and/or an organic acid salt, and having a pH of 3 or more and less than 4.

* * * * *